(12) United States Patent
Weber et al.

(10) Patent No.: US 9,827,096 B2
(45) Date of Patent: Nov. 28, 2017

(54) VALVULOPLASTY DEVICE

(71) Applicant: BOSTON SCIENTIFIC SCIMED, INC., Maple Grove, MN (US)

(72) Inventors: Jan Weber, Maastricht (NL); Aiden Flanagan, Co. Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/006,177

(22) Filed: Jan. 26, 2016

(65) Prior Publication Data

US 2016/0135949 A1  May 19, 2016

Related U.S. Application Data

(63) Continuation of application No. 13/772,594, filed on Feb. 21, 2013.
(Continued)

(51) Int. Cl.
  *A61B 17/22* (2006.01)
  *A61F 2/24* (2006.01)
  *A61B 17/00* (2006.01)

(52) U.S. Cl.
  CPC .............. *A61F 2/243* (2013.01); *A61B 17/22* (2013.01); *A61F 2/2427* (2013.01); *A61F 2/2475* (2013.01); *A61B 2017/00783* (2013.01); *A61B 2017/22098* (2013.01); *A61F 2/2412* (2013.01); *A61F 2/2433* (2013.01)

(58) Field of Classification Search
  CPC ...... A61F 2/243; A61F 2/2412; A61F 2/2427; A61F 2/2433; A61F 2/2475; A61B 2017/00783; A61B 2017/22098
  See application file for complete search history.

(56) References Cited

U.S. PATENT DOCUMENTS 5,456,667 A  10/1995  Ham et al.
8,192,479 B2  6/2012  Paul, Jr.
(Continued)

FOREIGN PATENT DOCUMENTS

WO  9101773 A1  2/1991
WO  2005007219 A2  1/2005
(Continued)

OTHER PUBLICATIONS

All foreign patent documents have been previously uploaded in parent U.S. Appl. No. 13/772,594, filed Feb. 21, 2013.
(Continued)

*Primary Examiner* — Thomas J Sweet
*Assistant Examiner* — Seema Mathew
(74) *Attorney, Agent, or Firm* — Seager, Tufte & Wickhem LLP (57) ABSTRACT

The disclosure pertains to valvuloplasty devices which include a first outer shaft, a second inner shaft, a plurality of elongate members disposed therebetween and adapted to be expanded radially by relative motion between the first outer shaft and second inner shaft and a circumferential member disposed about the central portions of the plurality of elongate members, wherein the circumferential member is urged by radial expansion of the plurality of elongate members to contact the valve to be treated thereby effecting a valvuloplasty and methods of use therefor.

14 Claims, 9 Drawing Sheets

Related U.S. Application Data (60) Provisional application No. 61/602,201, filed on Feb. 23, 2012.

(56) References Cited

U.S. PATENT DOCUMENTS

| | | | |
|---|---|---|---|
| 8,398,662 B2 | 3/2013 | Granada et al. | |
| 2006/0085022 A1* | 4/2006 | Hayes | A61M 25/104 606/192 |
| 2006/0229659 A1* | 10/2006 | Gifford | A61B 18/02 606/200 |
| 2007/0203503 A1* | 8/2007 | Salahieh | A61B 17/0644 606/108 |
| 2007/0287886 A1* | 12/2007 | Saadat | A61B 1/0008 600/115 |
| 2008/0015445 A1* | 1/2008 | Saadat | A61B 1/0008 600/470 |
| 2008/0058590 A1* | 3/2008 | Saadat | A61B 1/00085 600/109 |
| 2009/0143851 A1 | 6/2009 | Paul, Jr. | |
| 2009/0254165 A1* | 10/2009 | Tabor | A61F 2/2412 623/1.11 |
| 2009/0306582 A1 | 12/2009 | Granada et al. | |
| 2010/0094209 A1* | 4/2010 | Drasler | A61M 25/1002 604/95.04 |
| 2010/0179585 A1* | 7/2010 | Carpenter | A61F 2/013 606/200 |
| 2011/0118634 A1* | 5/2011 | Golan | A61B 17/22012 601/4 |
| 2012/0059366 A1* | 3/2012 | Drews | A61B 18/1492 606/33 |
| 2014/0018912 A1* | 1/2014 | Delaloye | A61F 2/2427 623/2.11 |
| 2014/0088634 A1* | 3/2014 | Sanati | A61F 2/013 606/200 |
| 2015/0306359 A1* | 10/2015 | Drasler | A61M 25/0108 606/191 |
| 2016/0158006 A1* | 6/2016 | Sandhu | A61F 2/2427 604/529 |
| 2016/0317276 A1* | 11/2016 | Groh | A61F 2/013 |
| 2017/0071460 A1* | 3/2017 | Miller | A61B 1/0008 |

FOREIGN PATENT DOCUMENTS

| | | |
|---|---|---|
| WO | 2007044285 A2 | 4/2007 |
| WO | 2008097999 A2 | 8/2008 |
| WO | 2008156468 A1 | 12/2008 |
| WO | 2011153408 A1 | 12/2011 |

OTHER PUBLICATIONS

PCT/US2013/027434, International Search Report dated Jun. 5, 2013.

* cited by examiner

VALVULOPLASTY DEVICE

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure pertains to a valvuloplasty catheter and methods of use therefor. In a first embodiment, the disclosure relates to a valvuloplasty device comprising a first elongate shaft having a longitudinal axis, a length, a proximal end, a distal end, and a lumen therebetween; a second elongate shaft slideably received within the lumen of the first elongate shaft having a proximal end and a distal end, wherein the second elongate shaft has a length greater than the length of the first elongate shaft; a plurality of elongate members each having a distal end, a proximal end and a central portion therebetween disposed between and operably connected at their proximal and distal ends to the first elongate shaft and the second elongate shaft; and a circumferential member disposed about the plurality of elongate members disposed between and operably connected to the first elongate shaft and the second elongate shaft, wherein the circumferential member is fixedly attached to the plurality of elongate members disposed between and operably connected to the first elongate shaft and the second elongate shaft, wherein a central portion of each elongate member of the plurality of elongate members disposed between and operably connected to the first elongate shaft and the second elongate shaft is fixedly attached to the circumferential member such that the plurality of elongate members disposed between and operably connected to the first elongate shaft and the second elongate shaft are distributed in a spaced-apart relationship about the circumferential member, further wherein the valvuloplasty device has a first configuration in which the distal end of the second elongate shaft extends distally beyond the distal end of the first elongate shaft and the plurality of elongate members disposed between and operably connected to the first elongate shaft and the second elongate shaft lie generally parallel to the longitudinal axis of the first elongate shaft and the valvuloplasty device has a second configuration in which the distal end of the second elongate shaft lies closer to the distal end of the first elongate shaft and the central portions of each elongate member of the plurality of elongate members disposed between and operably connected to the first elongate shaft and the second elongate shaft are adapted to extend radially outward from longitudinal axis of the first elongate shaft.

In a second embodiment, the disclosure relates to a method of performing a valvuloplasty, comprising inserting a valvuloplasty device intravascularly, said valvuloplasty device comprising an outer shaft; an inner shaft; a plurality of elongate members disposed between the distal end of the outer shaft and the distal end of the inner shaft; and a circumferential member affixed to the plurality of elongate members and disposed between the distal end of the outer shaft and the distal end of the inner shaft; advancing the valvuloplasty device to a position within the valve to be treated; reducing the distance between the distal end of the outer shaft and the distal end of the inner shaft thereby causing a central portion of the plurality of elongate members disposed between the distal end of the outer shaft and the distal end of the inner shaft to expand radially outward and press the circumferential member against the valve to be treated; increasing the distance between the distal end of the outer shaft and the distal end of the inner shaft thereby causing a central portion of the plurality of elongate members disposed between the distal end of the outer shaft and the distal end of the inner shaft to contract radially; removing the valvuloplasty device from the patient in a first configuration in which the distal end of the inner shaft extends distally beyond the distal end of the outer shaft and the plurality of elongate members disposed between and operably connected to the inner shaft and the outer shaft lie generally parallel to a longitudinal axis of the inner shaft.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary.

The valvuloplasty devices of the disclosure include a first elongate shaft and a second elongate shaft adapted for longitudinal motion relative to each other; a plurality of flexible elongate members operably affixed between the first elongate shaft and the second elongate shaft such that motion between the first elongate shaft and the second elongate shaft causes central portions of the plurality of elongate members to move in a radial direction; and a circumferential member surrounding the valvuloplasty device and attached to the central portions of the plurality of elongate members such that radial movement of the central portions of the flexible elongate members causes the circumferential member to engage the valve to be treated and radially expand said valve. The structure and operation of the valvuloplasty devices of this disclosure will be illustrated with reference to the following non-limiting examples. Throughout the disclosure, reference will be made to the embodiment of FIG. 1. It will be understood that features in figures which contain elements having like-numbered elements such as 120, 520, 720, and the like may be considered to illustrate details of the embodiment of FIG. 1 from which the features illustrated in the subsequent figures have been removed to reduce clutter.

Figure 1:
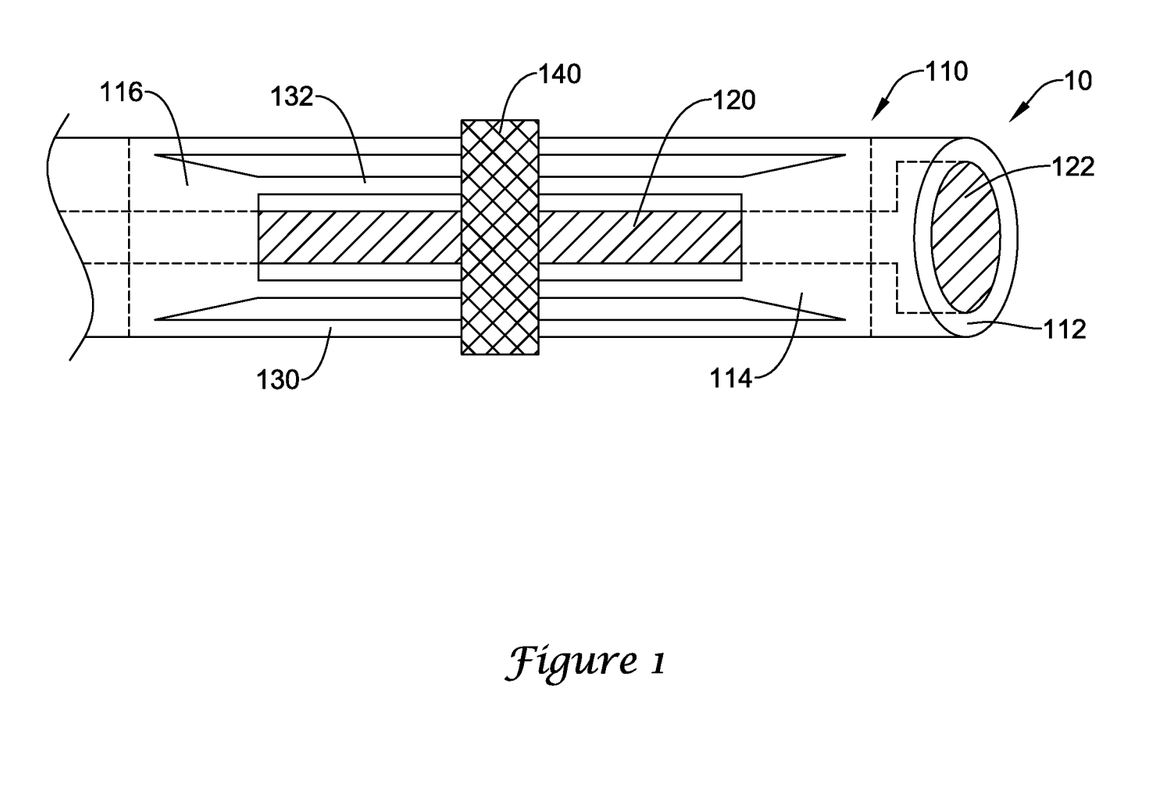
FIG. 1 illustrates a distal end region of a valvuloplasty device of the disclosure.

FIG. 1 illustrates an exemplary valvuloplasty device 10 comprising a first elongate shaft 110 having a longitudinal axis, a length, a proximal end (not shown), a distal end 112, and a lumen therebetween and a second elongate shaft 120 slideably received within the lumen of the first elongate shaft 110 having a proximal end (not shown) and a distal end 122. In some embodiments, the second shaft may include one or more lumens not visible in FIG. 1. Such additional lumens may include guidewire lumens, aspiration lumens, inflation/deflation lumens, infusion lumens, bypass lumens and the like. As illustrated in FIG. 1, the lumen of first elongate shaft 110 may provide significant clearance for the motion of second elongate shaft 120 therewithin to prevent binding as the valvuloplasty device flexes during insertion and retrieval; however the illustrated clearance may be significantly reduced.

Typically, the second elongate shaft 120 has a length greater than the length of the first elongate shaft 110 such that the proximal end of second elongate shaft 120 extends proximally with respect to the first elongate shaft 110 to allow manipulation of the two shafts; however in some embodiments (not shown), the first and second elongate shafts may terminate in a manipulation device such as a handle. If present, the handle may include elements which are adapted to move the proximal end of first elongate shaft 110 relative to the proximal end of second elongate shaft 120. Such elements may include levers, cams/cam followers, lead screws, or the like to provide mechanical advantage and/or precision control of the position of first elongate shaft 110 relative to second elongate shaft 120.

Figure 5:
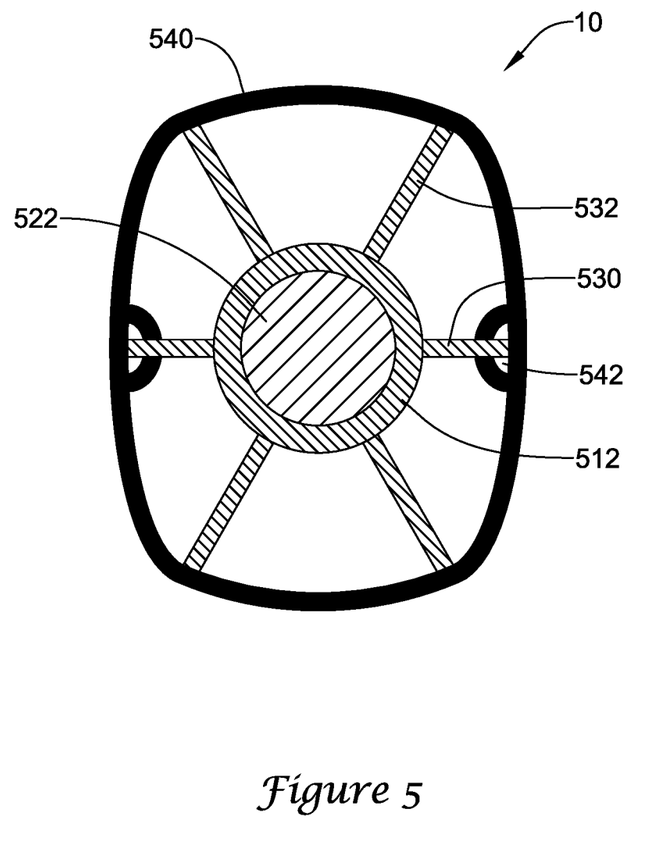
FIG. 5 illustrates schematically a distal end view of an embodiment of a valvuloplasty device of the disclosure.

In addition to first elongate shaft 110 and second elongate shaft 120, the valvuloplasty device 10 includes a plurality of elongate members disposed between and operably connected to the first elongate shaft and the second elongate shaft, said plurality of elongate members 130, 132 being disposed in a distal region of the valvuloplasty device 10 and operably positioned between the distal ends of first elongate shaft 110 and second elongate shaft 120. Although six elongate members have been illustrated in FIGS. 1, 5, and 6 to reduce clutter in the figures while illustrating features of the valvuloplasty device 10, more, or in some embodiments fewer, elongate members may be employed. Additionally, although two populations of elongate members 130, 132 have been illustrated, in other embodiments, 1, 3, 4, or more populations of elongate members may be employed within the plurality of elongate members depending upon the pressure profile and/or radial expansion profile to be achieved during the valvuloplasty.

It will be appreciated that in some embodiments, the plurality of elongate members 130, 132 may comprise elongate elements fixedly attached between the distal ends of the first elongate shaft 110 and second elongate shaft 120, while in other embodiments, the elongate members 130, 132 may be integrally formed from a distal region one of the elongate shafts 110, 120, for example by laser cutting of a tubular shaft, and fixedly attached to the other shaft by suitable means such as adhesives, welding, crimping, and the like. For the purposes of this disclosure, in those embodiments in which the plurality of elongate members 130, 132 are formed from a distal region of one of the elongate shafts 110, 120, the distal end of the elongate shaft thus modified will be understood to terminate proximally of the distal region and the plurality of elongate members 130, 132 within the distal region will be treated as separate elements attached to the distal end of the elongate shaft.

In certain embodiments (not shown), the plurality of elongate members may be of equal length. In certain other embodiments, the plurality of elongate members may include elongate members 130, 132 having distinct and differing lengths. In yet other embodiments, elongate members having 3, 4, or even more distinct lengths may be present if desired.

In addition to being optionally differentiated with regard to length, the individual elongate members of the plurality of elongate members may be differentiated with regard to cross-sectional area, cross-sectional shape and cross-sectional profile along their length. For example, in some embodiments individual elongate members may be of generally circular, oval, rectangular, or other cross-section and/or the cross-sectional shape may vary along the length of an individual elongate member. In other embodiments, mechanical properties may vary along the length of an elongate member. In yet other embodiments, at least some of the elongate members of the plurality of elongate members may be composite structures. A variety of biocompatible materials such as Nitinol, stainless steel, and polymers may be used alone or in combination to form the individual elongate members of the plurality of elongate members 130, 132. Although the illustrated exemplary embodiment employs relative motion between the first elongate shaft 110 and the second elongate shaft 120 to buckle the plurality of elongate members 130, 132 from a first configuration in which the plurality of elongate members lies generally parallel to the longitudinal axis of the valvuloplasty device to a second configuration in which the central portions of each elongate member of the plurality of elongate members 130, 132 extend radially outward from longitudinal axis of the valvuloplasty device 10, it will be appreciated that other actuation methods may be employed to effect the change of configuration or to initiate the buckling of the individual elongate members of the plurality of elongate members 130, 132.

For example, if the plurality of elongate members 130, 132 is formed, at least in part from shape memory materials, warming the plurality of elongate members 130, 132 may fully or partially expand the plurality of elongate members 130, 132 toward the second configuration. Although shape memory expansion may suffice to expand the valvuloplasty device 10 in some applications, it is anticipated that other applications will require additional expansion force which may be applied by manipulation of the first elongate shaft 110 and the second elongate shaft 120. In such embodiments, initial buckling of the plurality of elongate members 130, 132 may reduce the force required to further buckle the plurality of elongate members 130, 132 to the extent required for valvuloplasty. Other methods of initiating buckling may rely upon an expanding element illustrated schematically by segment 824A/824B of second elongate shaft 820 in FIG. 8. (Note that first elongate shaft, the plurality of elongate members, the circumferential member, and optional components such as the one-way valve of FIG. 7 have been omitted for clarity.) The expanding element may be, for example, an inflatable balloon which need only inflate locally and sufficiently to initiate buckling of the plurality of elongate members 130, 132, whereas full actuation of the valvuloplasty device 10 would typically require a relatively large volume of inflation fluid and an undesirably long inflation/deflation cycle. In some embodiments, initial deflection to initiate buckling may be facilitated mechanically and may either be provided by a permanently enlarged portion of second elongated shaft 820 such as a disk or bump resembling the profile presented as 824B or by any of the expansion devices commonly employed such as an umbrella-like mechanism.

Figure 2A:
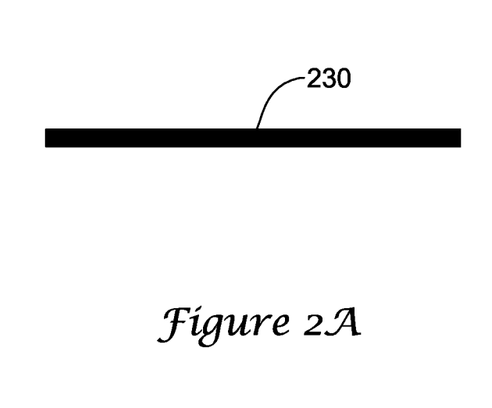
FIGS. 2A-2B illustrate schematically an exemplary elongate member in a first configuration and in a second configuration respectively.
Figure 2B:
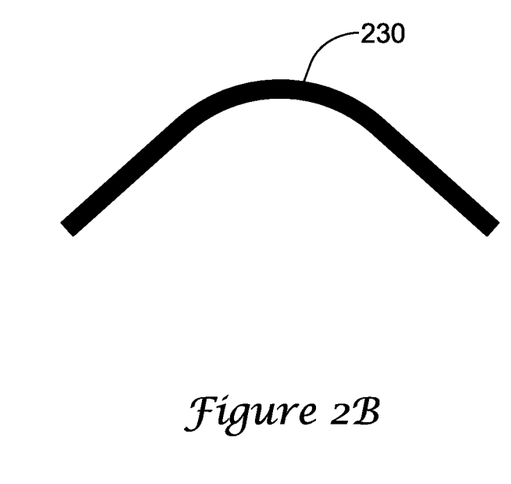
Figure 3A:
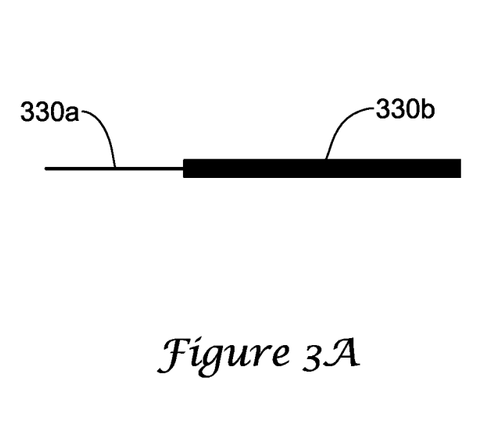
FIGS. 3A-3B illustrate schematically another exemplary elongate member in a first configuration and in a second configuration respectively.
Figure 3B:
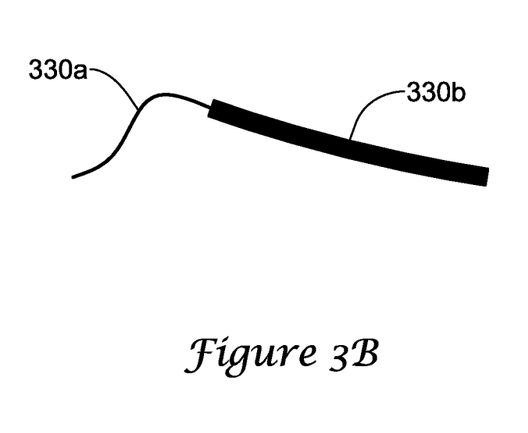
Figure 4A:
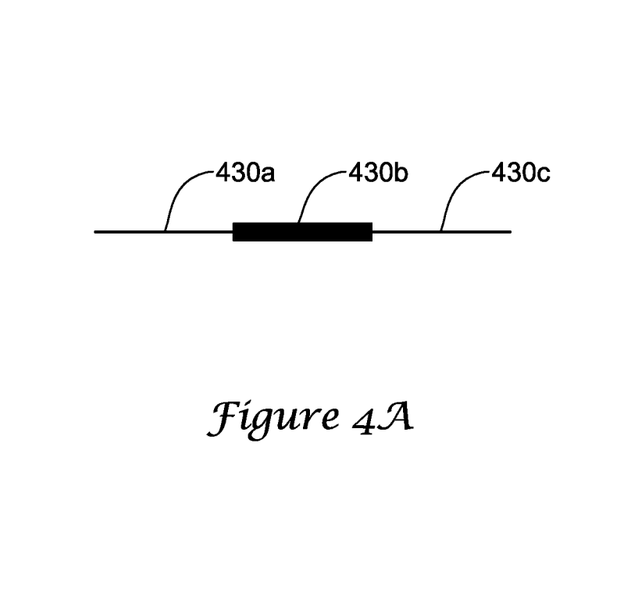
FIGS. 4A-4B illustrate schematically another exemplary elongate member in a first configuration and in a second configuration respectively.
Figure 4B:
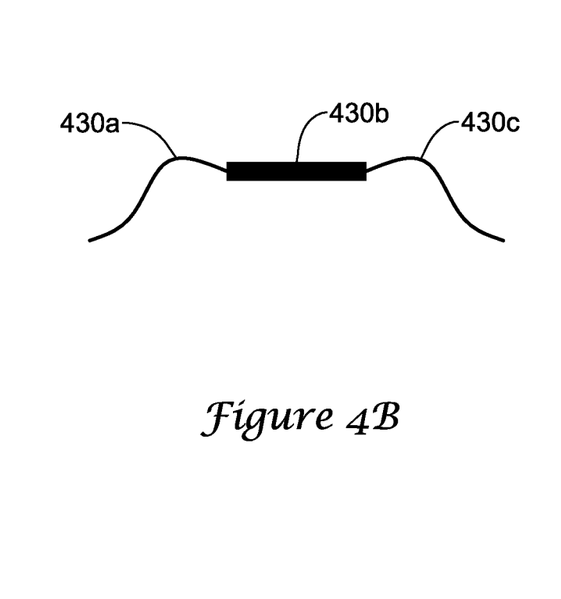

Turning to FIGS. 2, 3, and 4, a few non-limiting examples of individual elongate members will serve to illustrate the influence of these available variations upon the operation of a valvuloplasty device 10. FIG. 2A illustrates a substantially uniform elongate member 230 having moderate stiffness, for example a wire or ribbon. Relative motion between the first and second elongate shafts compresses the elongate member 230 causing it to buckle radially outward (FIG. 2B) such that the device as a whole expands radially to press outward on the valve to be treated.

In the embodiment of FIGS. 3A and 3B, the elongate member 330A/330B has two adjacent regions of differing stiffness in a radial direction such that longitudinal compression of the elongate member also causes a central portion of the elongate member to buckle radially outward as shown in FIG. 3B; however the differing stiffnesses of the regions, possibly in combination with the manner of attachment of the ends of the elongate member at the first and second elongate shafts, causes the stiffer region of the elongate member to assume an inclined orientation such that the expanded valvuloplasty device 10 as a whole has a taper which may better engage the leaflets of a valve within which the device is deployed and/or which may bias the device to move in a desired direction if it is displaced longitudinally during deployment. Although the illustrated embodiment of FIGS. 3A/3B suggests that the regions which differ with regard to stiffness have been produced by the presence of non-uniform thickness or diameter of the elongate member in two adjacent regions, it will be appreciated that a similar effect may be achieved by varying the width of the elongate member or the materials used in a composite elongate member. In other embodiments, a similar effect may be achieved by continuously tapering one or more regions of the elongate member rather than employing discrete sections of uniform cross-section. In still other embodiments, the different stiffness exhibited by adjacent regions 330A and 330B may be the result of differing orientations of a uniform cross-section. For example, if the elongate member 330A/330B is formed with a rectangular or oval cross-section, a 90 degree twist at the junction between regions 330A and 330B may produce the necessary dual stiffness. In region 330A, the wider dimension may be oriented to coincide with the circumferential direction, while in region 33B the wider dimension may be oriented to coincide with a radius of the device such that the difference in radial dimensions between the two regions produce different area moments of inertia and correspondingly different beam stiffnesses. Similarly, the addition of a rib to produce a "T" cross-section in region 33B may produce the desired change in the area moment of inertia of that region.

Figure 5A:
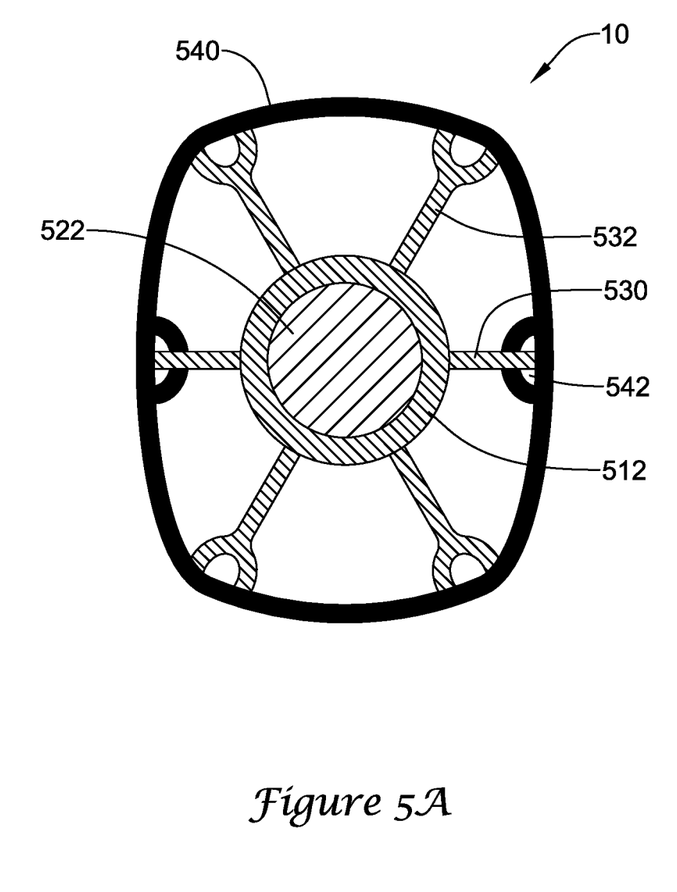
FIG. 5A illustrates schematically a distal end view of a variation of the embodiment of FIG. 5.
Figure 5B:
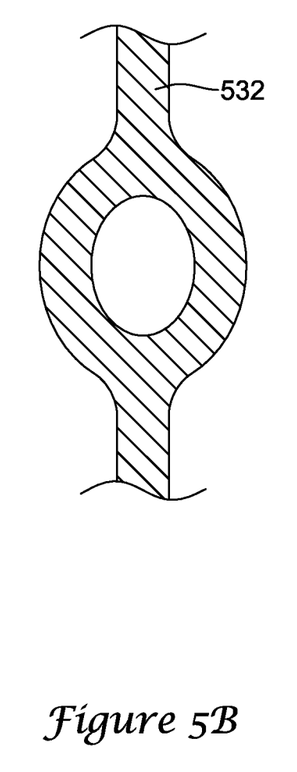
FIG. 5B illustrates a detail of the embodiment of FIG. 5A

In yet other embodiments, there may be more than two regions within an elongated member. In the embodiment of FIGS. 4A/4B/4C, three regions have been illustrated such that buckling of the elongate member is largely confined to regions 430A and 430C, while stiffer adjacent central region 430B remains largely undeformed and generally parallel to the longitudinal axes of the first and second elongate shafts. In such embodiments, sections 430A and 430C may be designed to extend radially outward farther than central region 430B and to cooperate with other elongate members of the plurality of elongate members to form retaining circumferential ridges which may tend to position the valvuloplasty device 10 within the valve to be treated. As discussed with regard to FIGS. 3A/3B, various alterations in the materials and geometries to the respective regions 4A, 4B, and 4C may be employed to create regions of differing stiffness along the length of an elongate member. It will be appreciated that additional regions of differing stiffness may be employed and that the transitions between regions may be gradual or step-wise transitions. In certain embodiments, for example that of FIG. 5A, elongate members having different configurations may be commingled.

Returning to FIG. 1, the exemplary embodiment also includes a circumferential member 140 disposed about the valvuloplasty device 10 within a region defined by and generally centrally located within a longitudinal region defined by distal and proximal ends of the plurality of elongate members 130, 132, where it surrounds the plurality of elongate members 130, 132 and is attached thereto. At least a portion of the circumferential member 140 lies outside of the plurality of elongate members 130, 132 when the elongate members 132 are disposed in a second configuration in which the members of the plurality of elongate members 130, 132 extend radially outward from longitudinal axis of the first elongate shaft.

In some embodiments, the circumferential member 140 is fixedly attached to each of the plurality of elongate members 130, 132, while in other embodiments the circumferential member 140 may be capable of limited motion with respect to the plurality of elongate members 130, 132. The plurality of elongate members 130, 132, in their radially expanded state, may be uniformly or non-uniformly distributed circumferentially with respect to the circumferential member 140. For example, the central portions of individual members of the plurality of elongate members 130, 132 may pass through elongated circumferential slots, best seen as slots 542 in FIG. 5, extending longitudinally through the circumferential member 140 such that the central portions of the individual members of the plurality of elongate members 130, 132 may be allowed limited freedom to distribute themselves circumferentially about the valvuloplasty device 10 in the second expanded configuration of the device. Some, all, or none of the points of contact between the circumferential member 540 and the individual members of the plurality of elongate members 130, 132 may be provided with such slots 542.

Similarly, some, all, or none of the points of contact between the circumferential member 540 and the individual members of the plurality of elongate members 130, 132 may fixedly attached, although typically at least some of the points of contact will be either fixedly attached or have limited circumferential movement. In certain embodiments, illustrated in FIG. 5A, some or all of the elongate members 530, 532 may include a widened contact region where the elongate members 530, 532 contact the circumferential member 540. It will be appreciated that a widened region may be added to any of the elongate members described herein to distribute contact pressure and/or to further shape the contact between a circumferential member and the valve to be dilated. In some embodiments (not shown), the circumferential member 140 will comprise a laminated inner component and an outer component such that the individual members of the plurality of elongate members 130, 132 may be sandwiched therebetween.

Additionally, the circumferential member 140 may usefully include a texture on the outermost surface thereof to enhance frictional engagement with the components of the valve to be expanded. In some embodiments, the circumferential member may be somewhat stiff such that it tends to remain somewhat circular or elliptical in the second expanded configuration shown in FIG. 5 from which some details have been omitted for clarity. In other embodiments, the elasticity of a circumferential member 140 may vary continuously of discretely around the circumference of the circumferential member 140 to better allow the circumferential member to adopt a desired shape, for example that of FIG. 6, in which the combination of two populations of elongate members 630, 632 and the mechanical properties of the circumferential member 640 produce a somewhat triangular shape which may be better suited for valvuloplasty of a tricuspid valve. In yet other embodiments, a circumferential member 140 may include reinforcing fibers, meshes, braids, or like selected to limit elastic expansion of regions of the circumferential member while retaining good flexibility. In certain embodiments, the circumferential member 140 may include a coating of appropriate drugs disposed therein or may include drugs dispersed therein to improve biocompatibility and/or for a therapeutic purpose. In certain other embodiments, other portions of the valvuloplasty device 10 may be coated with an appropriate drug or drugs to improve biocompatibility and/or for a therapeutic purpose.

As also illustrated in FIG. 1, the expansion region of a valvuloplasty device may also include one or both of distal collar 114 and proximal collar 116 which may include circumferential variations in longitudinal extent which may further combine with the lengths of the individual elongate members of the plurality of elongate members 130, 132 to determine the radial expansion which the individual elongate members of the plurality of elongate members 130, 132 may achieve. Collars 114, 116, like elongate members 130, 132, may comprise separate components which are assembled to create the valvuloplasty device 10, or may be formed as integrated components by selective removal of material from a distal region of one or both of the elongate shafts 110, 120. As illustrated in FIG. 1, the collars 114, 116 have been formed simultaneously with the plurality of elongate members 130, 132 by laser cutting, electromachining, or the like, from a distal tubular region of first elongate shaft 110. For the purposes of this disclosure, in those embodiments in which the collars 114, 116 are formed from a distal region of one of the elongate shafts 110, 120, the distal end of the elongate shaft thus modified will be understood to terminate proximally of the distal region and the collars 114, 116 formed within the distal region will be treated as separate elements attached to the distal end of the elongate shaft and to the plurality of elongate members.

In other embodiments, one or both of collars 114, 116, if present, may be formed separately and fixedly attached proximate distal end 122 of second elongate shaft 120 or proximate distal end of first elongate shaft 110. In such embodiments, the individual elongate members of the plurality of elongate members 130, 132 may either be formed separately and fixedly attached to the respective collars 114, 116 or to the distal ends of first and second elongate shafts or, in other embodiments, may be formed integrally with one or both of the respective collars 114, 116 and later assembled to form the valvuloplasty device by fixedly attaching the free end of each elongate member to either an opposed collar or shaft end. In some embodiments, the individual collars 114, 116 may comprise only one or more extensions from a first elongate shaft end or second elongate shaft end. Typically collars 114, 116 will be constructed such that the midpoints of the individual elongate members of the plurality of elongate members 130, 132 will fall on a transverse plane through the valvuloplasty device; however in certain embodiments, the midpoints of subsets of the plurality of elongate members 130, 132 may fall on more than one transverse plane. If desired, the transverse plane(s) may lie at an angle other than a right angle with respect to the second elongate shaft to better align the circumferential member 140 within the valve.

In certain embodiments (not shown) asymmetric elongate members, such as elongate members 330A/33B, may be arranged such that regions 330A of a portion of the elongate members and regions 33B of adjacent elongate members alternate in their connection to the respective distal and proximal collars 114, 116, if present, or to the appropriate portions of elongate shafts 110, 120, to provide radially expanded regions both distal and proximal of the circumferential band 140 which may tend to center the circumferential member within the valve.

Figure 6:
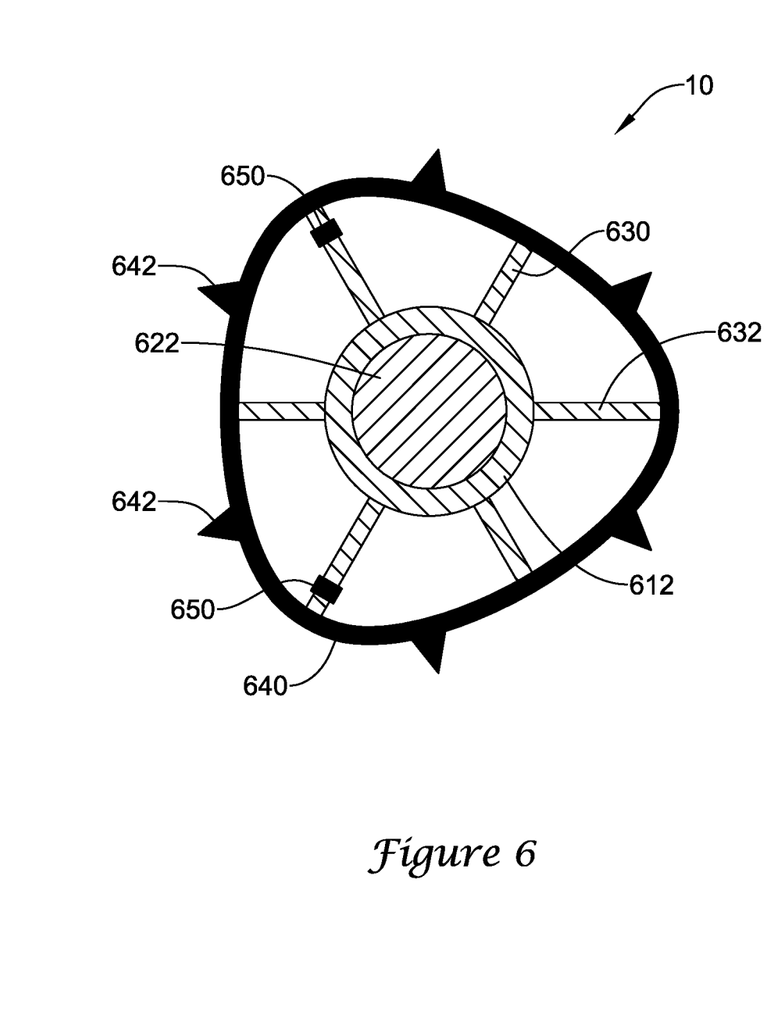
FIG. 6 illustrates schematically a distal end view of another embodiment of a valvuloplasty device of the disclosure.

As further illustrated in FIG. 6, each embodiment of the disclosed valvuloplasty device optionally may include one or more visualization aids 650, such as radiopaque visualization aids and/or MM visualization aids to facilitate correct positioning of the valvuloplasty device. Such visualization aids may be provided in any of the forms known in the art such as by, for example, gold plating, or by wrapping a visualization material around a portion of the device. Although the visualization aids 650 of FIG. 6 are illustrated as attached to elongate members, it will be appreciated that the purpose may be served by visualization aids attached to various other portions of the device. The visualization aids of FIG. 6 are attached to elongate members in an asymmetric pattern to facilitate rotation positioning as well as longitudinal positioning within, for example, a tricuspid valve.

As also illustrated in FIG. 6, each embodiment of the disclosed valvuloplasty device optionally may include one or more cutting edges 642 extending radially outward therefrom. Such cutting edges may be associated with circumferential member 640 and/or individual members of the plurality of elongate members. Such cutting edges may serve to partially relieve any adhesions associated with the valve components, to partially break up calciferous buildup on the valve components, and/or to enlarge the opening left following treatment of the valve.

While the disclosed valvuloplasty devices may provide a relatively non-occlusive alternative to the occlusive balloon catheters of the prior art and thus may avoid the complications associated with long duration expansions of the valve to be treated, during the treatment of certain valves within the body it may be desirable during the valvuloplasty to provide the one-way valve action of the valve being treated or replaced, thereby allowing a measure of near normal blood flow and/or to provide pulsate pressure relief within the structure being treated while preventing regurgitation. In such circumstances a one-way valve, exemplified in FIG. 7 as element 760, may be provided about the second elongate shaft 720 and affixed at circumferential rim 762 to a circumferential member (first elongate shaft, the plurality of elongate members, and the circumferential member are not shown for clarity). As illustrated, one-way valve 760 tapers from circumferential rim 762 to a rim 764 which allows the valve to close about second elongate shaft 720, thereby sealing the lumen formed by the deployed valvuloplasty device 10 against retrograde flows. One-way valve 760 typically is made from a flexible and/or elastomeric biocompatible polymer such as a polyurethane. The one-way valve 760 may have 1, 2, 3, 4, or more generally longitudinal slits 766 disposed around the circumference of the valve element such that the slits may open as the one-way valve 760 is displaced from contact with the second elongated shaft 720 during periods of fluid flow and may close as one-way valve 760 is subjected to retrograde flows. Although the slits have been depicted as extending through rim 764, it will be appreciated that they need not do so. Leaving the rim 764 intact may tend to prevent leakage and may better maintain the position of the valve within the device.

Figure 7:
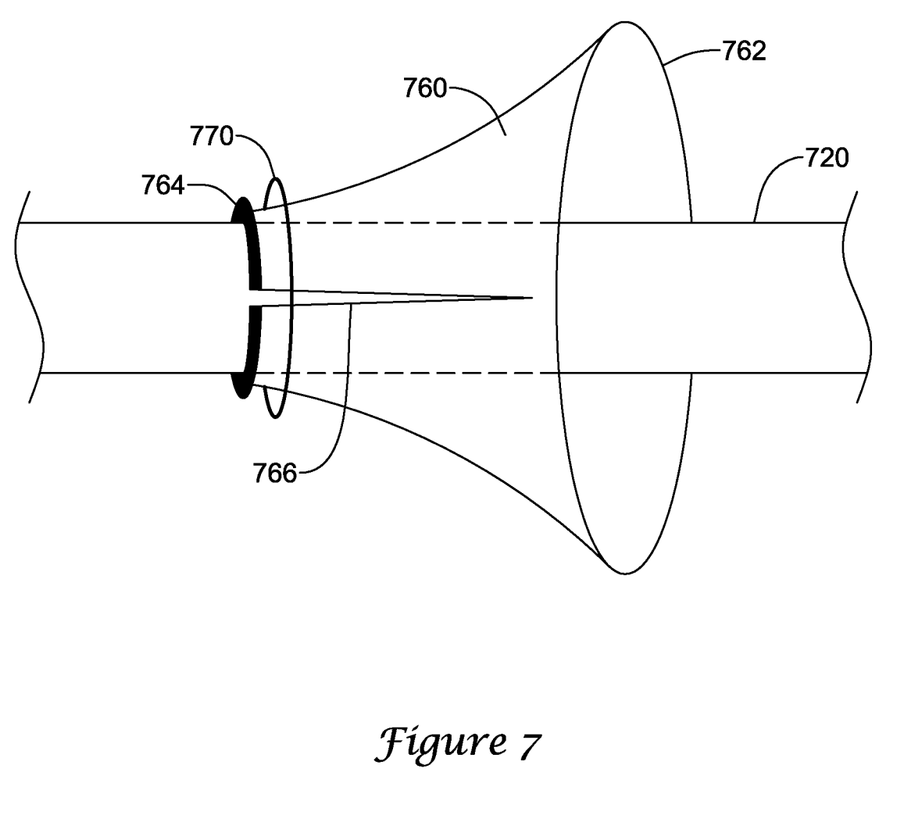
FIG. 7 illustrates a one-way valve which may be employed with any of the embodiments of the disclosure.

The one-way valve of FIG. 7 may optionally include a retainer, such as ring 770 which serves to prevent inversion/eversion of the one-way valve, or portions thereof, during retrograde flows. In other embodiments, other retaining devices such as tethers connecting rim 764 segments to second elongated shaft 720 may be employed. In yet other embodiments, the one-way valve 760 may include ribs or other stiffening elements which serve a similar purpose. It will be appreciated that other one-way valve structures, for example one or more reed valves, may be substituted for the non-limiting exemplary one-way valve 760. It will be further appreciated that a one-way valve may be incorporated in each of the valvuloplasty device embodiments disclosed herein.

The valvuloplasty device 10 of the disclosure may be advanced intravascularly by conventional pathways to a position within the valve to be treated. Proper positioning may be confirmed by imaging the radiopaque or Mill visualization aids 650 or their equivalents. Once positioned within the valve to be treated, one or both of the first outer elongate shaft and the second inner elongate shaft may be moved to decrease the distance between the proximal and distal ends of the plurality of elongate members thereby causing a central portion of the plurality of elongate members 130, 132 to buckle and expand radially outward to press the circumferential member 140 against the valve to be treated. As described herein levers, cams/cam followers, lead screws, or the like may be used to move one or both of the first outer elongate shaft 110 and the second inner elongate shaft 120 to provide mechanical advantage and/or precision control of the position of first elongate shaft 110 relative to second elongate shaft 120. It will be appreciated that the radial expansion of the elongate members 130, 132 may be accomplished in a single stage or may be accomplished in steps with pauses at one or more expanded diameters.

Figure 8:
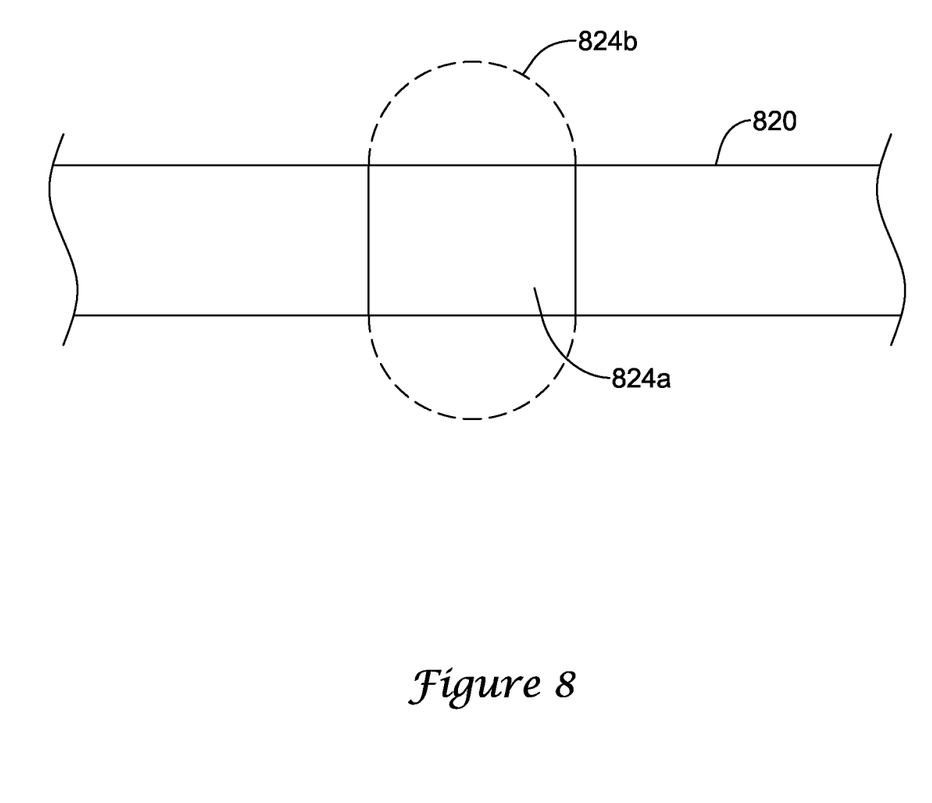
FIG. 8 illustrates schematically a radially expandable element which may be employed with any of the embodiments of the disclosure, said radially expandable element being adapted to urge the circumferential members radially outward

Also as disclosed herein, each of the disclosed embodiments of the valvuloplasty device may optionally include one or more radially expandable elements 824B or radially extended fixed elements (not shown) to provide initial radial displacement of a central portion of the plurality of elongate members 130, 132 prior to, or concurrent with, decreasing the distance between the proximal and distal ends of the plurality of elongate members 130, 132 thereby facilitating buckling of the plurality of elongate members 130, 132 with a lower longitudinally applied force.

Any of the valvuloplasty devices 10 of the disclosure may, as noted herein, include one-way valves 760 which are adapted to span an aperture defined by the circumferential member in a second radially extended configuration. It is contemplated that some such one-way valves 760 may include a retainer or retainers 770 which serve to prevent inversion/eversion and further that some such retainers 770 may be actuatable (not shown) to move the one-way valve 760 from a first configuration in which the one-way valve 760 is held closed and a second configuration in which the one-way valve 760 is free to respond to pressure differentials across the one-way valve 760 in the conventional manner. In valvuloplasty devices 10 which include both a one-way valve 760 and retainer(s) 770, the one-way valves 760 may be allowed to operate at appropriate times during the valvuloplasty procedure.

Any of the valvuloplasty devices 10 of the disclosure may, as noted herein, include one or more cutting edges, for example 642, associated with a circumferential member, such as 640, or with one or more elongate members, for example 630 and/or 632, or both. When a valvuloplasty device 10 is so equipped, radial expansion of the elongate members may cause one or more cutting edges 642 to cut the valve being treated and/or the surrounding tissue. Additionally or in the alternative, longitudinal and/or rotational motion of the valvuloplasty device 10 in a radially expanded configuration or a partially radially expanded configuration may result in further cutting or scraping of the valve being treated and/or the surrounding tissue.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:
1. A method of performing a valvuloplasty, comprising:
inserting a valvuloplasty device intravascularly into a patient,
said valvuloplasty device comprising:
an outer shaft;
an inner shaft;

a plurality of elongate members disposed between the distal end of the outer shaft and the distal end of the inner shaft and affixed thereto;

and a circumferential member affixed to the plurality of elongate members and disposed between the distal end of the outer shaft and the distal end of the inner shaft;

advancing the valvuloplasty device to a position within a valve to be treated;

reducing a distance between the distal end of the outer shaft and the distal end of the inner shaft thereby causing a central portion of the plurality of elongate members disposed between the distal end of the outer shaft and the distal end of the inner shaft to expand to a radially expanded configuration and press the circumferential member against the valve to be treated thereby performing a valvuloplasty;

increasing the distance between the distal end of the outer shaft and the distal end of the inner shaft thereby causing the central portion of the plurality of elongate members disposed between the distal end of the outer shaft and the distal end of the inner shaft to contract radially;

removing the valvuloplasty device from the patient intact in a radially contracted configuration in which the distal end of the inner shaft extends distally beyond the distal end of the outer shaft and the plurality of elongate members disposed between and operably connected to the inner shaft and the outer shaft are generally parallel to a longitudinal axis of the inner shaft.

2. The method of claim 1, wherein the valvuloplasty device includes one or more cutting edges extending radially outward therefrom and the step of reducing the distance between the distal end of the outer shaft and the distal end of the inner shaft causes the central portion of the plurality of elongate members disposed between the distal end of the outer shaft and the distal end of the inner shaft to expand radially outward and causes the one or more cutting edges extending radially outward to cut the valve to be treated.

3. The method of claim 1, wherein the valvuloplasty device includes a first population of elongate members and a second population of elongate members, wherein the first population of elongate members differs from the second population of elongate members with regard to lengths of the members of the respective populations of elongate members.

4. The method of claim 1, wherein the valvuloplasty device includes a first population of elongate members and a second population of elongate members, wherein the first population of elongate members differs from the second population of elongate members with regard to the stiffness of the elongate members of the respective populations.

5. The method of claim 1, wherein the valvuloplasty device includes elongate members which vary in cross-sectional area along their length.

6. The method of claim 1, wherein the valvuloplasty device includes elongate members which vary in cross-sectional shape along their length.

7. The method of claim 1, wherein the valvuloplasty device includes elongate members which vary with regard to a mechanical property along their length.

8. The method of claim 1, wherein the plurality of elongate members are uniformly distributed circumferentially in the radially expanded configuration.

9. The method of claim 1, wherein the plurality of elongate members are non-uniformly distributed circumferentially in the radially expanded configuration.

10. The method of claim 1, wherein the radially expanded configuration includes a longitudinal taper.

11. The method of claim 1, wherein the circumferential member is textured on its radially outermost surface.

12. The method of claim 1, wherein the valvuloplasty device includes a drug coating on at least a portion of its surface.

13. The method of claim 1, wherein the valvuloplasty device includes a one-way valve.

14. The method of claim 1, wherein the valvuloplasty device includes a one or more radiopaque elements.

* * * * *